US009139618B2

(12) United States Patent
Villoing

(10) Patent No.: US 9,139,618 B2
(45) Date of Patent: Sep. 22, 2015

(54) SALMONID ALPHAVIRUS PROTEIN E2

(75) Inventor: Stephane Villoing, Ulset (NO)

(73) Assignee: Intervet Inc., Madison, NJ (US)

( * ) Notice: Subject to any disclaimer, the term of this patent is extended or adjusted under 35 U.S.C. 154(b) by 76 days.

(21) Appl. No.: 13/976,265

(22) PCT Filed: Dec. 28, 2011

(86) PCT No.: PCT/EP2011/074121
§ 371 (c)(1),
(2), (4) Date: Jun. 26, 2013

(87) PCT Pub. No.: WO2012/089749
PCT Pub. Date: Jul. 5, 2012

(65) Prior Publication Data
US 2013/0337007 A1    Dec. 19, 2013

Related U.S. Application Data

(60) Provisional application No. 61/430,299, filed on Jan. 6, 2011.

(30) Foreign Application Priority Data

Dec. 29, 2010    (EP) .................................... 10197232

(51) Int. Cl.
| *C07K 14/005* | (2006.01) |
| *A61K 39/295* | (2006.01) |
| *A61K 39/12* | (2006.01) |
| *C12N 7/00* | (2006.01) |
| *A61K 39/00* | (2006.01) |

(52) U.S. Cl.
CPC .............. *C07K 14/005* (2013.01); *A61K 39/12* (2013.01); *A61K 39/295* (2013.01); *C12N 7/00* (2013.01); *A61K 2039/552* (2013.01); *A61K 2039/55566* (2013.01); *C12N 2770/36122* (2013.01); *C12N 2770/36134* (2013.01); *C12N 2770/36151* (2013.01)

(58) Field of Classification Search
None
See application file for complete search history.

(56) References Cited

U.S. PATENT DOCUMENTS

| 6,719,980 B1 * | 4/2004 | Weston et al. ............. 424/218.1 |
| 6,936,256 B2 * | 8/2005 | Vakharia .................... 424/204.1 |
| 2013/0337007 A1 * | 12/2013 | Villoing .................... 424/201.1 |

FOREIGN PATENT DOCUMENTS

| EP | 0 712 926 A2 | 5/1996 |
| WO | 99/58639 A2 | 5/1999 |
| WO | 2007/031572 A1 | 3/2007 |

OTHER PUBLICATIONS

Moriette et al., (Journal of General Virology. 2005;86:3119-3127).*
Wickham et al., (Biotechnology Progress. 1992;8:391-396).*
Kost et al., (Nature Biotechnology; 2005; 23(5):567-575).*
Biering et al., "Update on Viral Vaccines for Fish", Developments in Biologicals, Karger, Basel, 2005, pp. 97-113, vol. 121.
Chen et al., "Cooperative effects of urea and L-arginine on protein refolding", Protein Expression and Purification, 2009, pp. 82-90, vol. 66.
Das et al., "Immunological evaluation of *Escherichia coli* expressed E2 protein of Western equine encephalitis virus", Virus Research, 2007, pp. 26-33, vol. 128.
Hodneland et al., "New subtype of salmonid alphavirus (SAV), Togaviridae, from Atlantic salmon *Salmo salar* and rainbow trout *Oncorhynchus mykiss* in Norway", Diseases of Aquatic Organisms, 2005, pp. 113-120, vol. 66.
Hodneland et al., Database UniProt [Online], Database Accession No. Q53AM6, Abstract, XP-002638312, May 20, 2011, found at http://ibis.internal.epo.org/IBIS/exam/dbfetch.jsp?id=UNIPROT:Q . . . .
Hu et al., "Cloning, expression and purification of envelope proteins E1 and E2 of western equine encephalitis virus and potential use of them as antigens in immunoassays", Veterinary Microbiology, 2008, pp. 374-379, vol. 128.
Tsumoto et al., "Role of Arginine in Protection Refolding, Solubilization, and Purification", Biotechnol. Prog., 2004, pp. 1301-1308, vol. 20.
European Search Report for EP 10 19 7232, dated Jun. 8, 2011.
International Search Report for PCT/EP2011/074121, mailed on May 3, 2012.

* cited by examiner

*Primary Examiner* — Shanon A Foley

(57) ABSTRACT

The present invention relates to Salmonid alphavirus E2-protein expressed in a bacterial expression system, its use in medicine, vaccines comprising such protein, methods for the preparation of such proteins and methods for the preparation of vaccines comprising such proteins.

19 Claims, No Drawings

SEQUENCE LISTING

```
<160> NUMBER OF SEQ ID NOS: 14

<210> SEQ ID NO 1
<211> LENGTH: 31
<212> TYPE: DNA
<213> ORGANISM: salmonid alphavirus

<400> SEQUENCE: 1
ccgcgcgagc ccctggtatg caacacagtg c                                31

<210> SEQ ID NO 2
<211> LENGTH: 33
<212> TYPE: DNA
<213> ORGANISM: salmonid alphavirus

<400> SEQUENCE: 2
ataccagggg ctcgcgcctc gagaccctac ttg                              33
```

```
<210> SEQ ID NO 3
<211> LENGTH: 33
<212> TYPE: DNA
<213> ORGANISM: salmonid alphavirus

<400> SEQUENCE: 3
gatgccataa gcttgacacg cgctccggcc ctc                           33

<210> SEQ ID NO 4
<211> LENGTH: 28
<212> TYPE: DNA
<213> ORGANISM: salmonid alphavirus

<400> SEQUENCE: 4
cgtcactttc accagcgact cccagacg                                 28

<210> SEQ ID NO 5
<211> LENGTH: 29
<212> TYPE: DNA
<213> ORGANISM: salmonid alphavirus

<400> SEQUENCE: 5
ggatccattc ggatgtggcg ttgctatgg                                29

<210> SEQ ID NO 6
<211> LENGTH: 35
<212> TYPE: DNA
<213> ORGANISM: salmonid alphavirus

<400> SEQUENCE: 6
ccctcctgct gctgcatatg gttattgtct gcacc                         35

<210> SEQ ID NO 7
<211> LENGTH: 35
<212> TYPE: DNA
<213> ORGANISM: salmonid alphavirus

<400> SEQUENCE: 7
ggtgcagaca ataaccatat gcagcagcag gaggg                         35

<210> SEQ ID NO 8
<211> LENGTH: 41
<212> TYPE: DNA
<213> ORGANISM: salmonid alphavirus

<400> SEQUENCE: 8
gcatacctgg ggctcgtgcg tgacaaccct acctggacat c                  41

<210> SEQ ID NO 9
<211> LENGTH: 41
<212> TYPE: DNA
<213> ORGANISM: salmonid alphavirus

<400> SEQUENCE: 9
gatgtccagg tagggttgtc acgcacgagc cccaggtatg c                  41

<210> SEQ ID NO 10
<211> LENGTH: 19
<212> TYPE: DNA
<213> ORGANISM: salmonid alphavirus

<400> SEQUENCE: 10
aatacgactc actataggg                                           19
```

-continued

```
<210> SEQ ID NO 11
<211> LENGTH: 19
<212> TYPE: DNA
<213> ORGANISM: salmonid alphavirus

<400> SEQUENCE: 11
gctagttatt gctcagcgg                                                    19

<210> SEQ ID NO 12
<211> LENGTH: 1611
<212> TYPE: DNA
<213> ORGANISM: salmonid alphavirus
<220> FEATURE:
<221> NAME/KEY: CDS
<222> LOCATION: (1)..(1512)

<400> SEQUENCE: 12 gga gat ata cat atg gtg att gtc tgc acc tac aac tcc aac acc ttt       48
Gly Asp Ile His Met Val Ile Val Cys Thr Tyr Asn Ser Asn Thr Phe
1               5                   10                  15 gat tgc tcc aaa ccg tcc tgc cag gac tgt tgt atc act gct gaa cca       96
Asp Cys Ser Lys Pro Ser Cys Gln Asp Cys Cys Ile Thr Ala Glu Pro
            20                  25                  30 aag aag gcc atg gct atg ttg aag g

| | | |
|---|---|---|
| tac ctc gtt gac gtg tac gac gct ctg ccg att tct gta gag att agc<br>Tyr Leu Val Asp Val Tyr Asp Ala Leu Pro Ile Ser Val Glu Ile Ser<br>245 250 255 | | 768 |
| acc gtt gta aca tgc aac gac aat cag tgc aca gtg agg gtg tca ccc<br>Thr Val Val Thr Cys Asn Asp Asn Gln Cys Thr Val Arg Val Ser Pro<br>260 265 270 | | 816 |
| ggt acc aca gtg aaa ttc gat aag aag tgc aag agc gct gcc caa gcg<br>Gly Thr Thr Val Lys Phe Asp Lys Lys Cys Lys Ser Ala Ala Gln Ala<br>275 280 285 | | 864 |
| acc gtt acc ttt acc agc gac tcc cag acg ttt acg tgt gag gag ccg<br>Thr Val Thr Phe Thr Ser Asp Ser Gln Thr Phe Thr Cys Glu Glu Pro<br>290 295 300 | | 912 |
| gtt ctg acg gcc gcc agt atc acc cag ggc aag ccg cac ctt aga tca<br>Val Leu Thr Ala Ala Ser Ile Thr Gln Gly Lys Pro His Leu Arg Ser<br>305 310 315 320 | | 960 |
| tct atg ttg ccc agc gga ggc aag gaa gtg aag gcg agg atc cca ttc<br>Ser Met Leu Pro Ser Gly Gly Lys Glu Val Lys Ala Arg Ile Pro Phe<br>325 330 335 | | 1008 |
| ccg ttc ccg cca gag acc gcg acc tgc aga gta agt gtc gcc ccg ctg<br>Pro Phe Pro Pro Glu Thr Ala Thr Cys Arg Val Ser Val Ala Pro Leu<br>340 345 350 | | 1056 |
| ccg tcg atc acc tat gag gaa agc gac gtt ctg ctg gcc ggt acc gcg<br>Pro Ser Ile Thr Tyr Glu Glu Ser Asp Val Leu Leu Ala Gly Thr Ala<br>355 360 365 | | 1104 |
| aag tac ccc gtg ctg ctg act aca cgg aac ctt ggt ttc cac agc aat<br>Lys Tyr Pro Val Leu Leu Thr Thr Arg Asn Leu Gly Phe His Ser Asn<br>370 375 380 | | 1152 |
| gcc aca tcc gaa tgg atc cag ggt aag tac ttg cgc cgt atc ccg gtc<br>Ala Thr Ser Glu Trp Ile Gln Gly Lys Tyr Leu Arg Arg Ile Pro Val<br>385 390 395 400 | | 1200 |
| acg ccc caa ggg atc gaa cta acg tgg gga aat aac gca ccg ttg cac<br>Thr Pro Gln Gly Ile Glu Leu Thr Trp Gly Asn Asn Ala Pro Leu His<br>405 410 415 | | 1248 |
| ttc tgg tca tct gtt agg tac gca tct ggg gac gcc gac gcg tac cct<br>Phe Trp Ser Ser Val Arg Tyr Ala Ser Gly Asp Ala Asp Ala Tyr Pro<br>420 425 430 | | 1296 |
| tgg gaa ctt ctg gtg cac cac acc aag cac cat ccg gag tac gcg tgg<br>Trp Glu Leu Leu Val His His Thr Lys His His Pro Glu Tyr Ala Trp<br>435 440 445 | | 1344 |
| gcg ttt gta gga gtt gca tgt ggt ctg ctg gtt att gca gta tgc atg<br>Ala Phe Val Gly Val Ala Cys Gly Leu Leu Val Ile Ala Val Cys Met<br>450 455 460 | | 1392 |
| ttc gcg tgc gca tgc aac aga gtg cgg tac tct ttg gtc gcc aac acg<br>Phe Ala Cys Ala Cys Asn Arg Val Arg Tyr Ser Leu Val Ala Asn Thr<br>465 470 475 480 | | 1440 |
| ttc aac ccg aac cca cca ctg acc gca ctg act gca gca ttg tgc<br>Phe Asn Pro Asn Pro Pro Leu Thr Ala Leu Thr Ala Ala Leu Cys<br>485 490 495 | | 1488 |
| tgc ata cct ggg gct cgt gcg tga caacccctacc tggacatcat tgcctacttg<br>Cys Ile Pro Gly Ala Arg Ala<br>500 | | 1542 |
| tggaagggcg aattctgcag atatccatca cactggcggc cgctcgagca ccaccaccac | | 1602 |
| caccactga | | 1611 |

<210> SEQ ID NO 13
<211> LENGTH: 503
<212> TYPE: PRT
<213> ORGANISM: salmonid alphavirus

```
<400> SEQUENCE: 13

Gly Asp Ile His Met Val Ile Val Cys Thr Tyr Asn Ser Asn Thr Phe
1               5                   10                  15

Asp Cys Ser Lys Pro Ser Cys Gln Asp Cys Cys Ile Thr Ala Glu Pro
            20                  25                  30

Lys Lys Ala Met Ala Met Leu Lys Asp Asn Leu Asn Asp Pro Asn Tyr
            35                  40                  45

Trp Asp Leu Leu Ile Ala Val Thr Thr Cys Asn Ser Ala Arg Lys Lys
    50                  55                  60

Arg Ala Val Ser Thr Ser Pro Ala Ala Val Tyr Asp Thr Gln Ile Leu
65                  70                  75                  80

Ala Ala His Ala Ala Ala Ser Pro Tyr Arg Ala Tyr Cys Pro Asp Cys
                85                  90                  95

Asp Gly Thr Ala Cys Ile Ser Pro Ile Ala Ile Asp Glu Val Val Ser
            100                 105                 110

Ser Gly Ser Asp His Val Leu Arg Ile Arg Val Gly Ser Gln Ser Gly
            115                 120                 125

Val Thr Ala Lys Gly Gly Ala Ala Gly Glu Thr Ser Leu Arg Tyr Leu
130                 135                 140

Gly Arg Asp Gly Lys Val His Ala Ala Asp Asn Thr Arg Leu Val Val
145                 150                 155                 160

Arg Thr Thr Ala Lys Cys Asp Val Leu Gln Ala Thr Gly His Tyr Ile
                165                 170                 175

Leu Ala Ser Cys Pro Glu Gly Gln Ser Ile Thr Val Ala Ala Thr Leu
            180                 185                 190

Asp Gly Thr Arg His Gln Cys Thr Val Phe Glu His Gln Val Thr
            195                 200                 205

Glu Lys Phe Thr Arg Glu Arg Ser Lys Gly His His Leu Ser Asp Leu
210                 215                 220

Thr Lys Lys Cys Thr Arg Phe Ser Thr Thr Pro Lys Lys Ser Ala Pro
225                 230                 235                 240

Tyr Leu Val Asp Val Tyr Asp Ala Leu Pro Ile Ser Val Glu Ile Ser
            245                 250                 255

Thr Val Val Thr Cys Asn Asp Asn Gln Cys Thr Val Arg Val Ser Pro
            260                 265                 270

Gly Thr Thr Val Lys Phe Asp Lys Lys Cys Lys Ser Ala Ala Gln Ala
            275                 280                 285

Thr Val Thr Phe Thr Ser Asp Ser Gln Thr Phe Thr Cys Glu Glu Pro
290                 295                 300

Val Leu Thr Ala Ala Ser Ile Thr Gln Gly Lys Pro His Leu Arg Ser
305                 310                 315                 320

Ser Met Leu Pro Ser Gly Gly Lys Glu Val Lys Ala Arg Ile Pro Phe
            325                 330                 335

Pro Phe Pro Pro Glu Thr Ala Thr Cys Arg Val Ser Val Ala Pro Leu
            340                 345                 350

Pro Ser Ile Thr Tyr Glu Glu Ser Asp Val Leu Leu Ala Gly Thr Ala
            355                 360                 365

Lys Tyr Pro Val Leu Leu Thr Thr Arg Asn Leu Gly Phe His Ser Asn
            370                 375                 380

Ala Thr Ser Glu Trp Ile Gln Gly Lys Tyr Leu Arg Arg Ile Pro Val
385                 390                 395                 400

Thr Pro Gln Gly Ile Glu Leu Thr Trp Gly Asn Asn Ala Pro Leu His
                405                 410                 415
```

```
Phe Trp Ser Ser Val Arg Tyr Ala Ser Gly Asp Ala Asp Ala Tyr Pro
            420                 425                 430

Trp Glu Leu Leu Val His His Thr Lys His His Pro Glu Tyr Ala Trp
        435                 440                 445

Ala Phe Val Gly Val Ala Cys Gly Leu Leu Val Ile Ala Val Cys Met
        450                 455                 460

Phe Ala Cys Ala Cys Asn Arg Val Arg Tyr Ser Leu Val Ala Asn Thr
465                 470                 475                 480

Phe Asn Pro Asn Pro Pro Leu Thr Ala Leu Thr Ala Ala Leu Cys
                485                 490                 495

Cys Ile Pro Gly Ala Arg Ala
            500

<210> SEQ ID NO 14
<211> LENGTH: 10
<212> TYPE: PRT
<213> ORGANISM: salmonid alphavirus

<400> SEQUENCE: 14

Thr Arg Ala Pro Ala Leu Leu Leu Leu Pro
1               5                   10
```

SALMONID ALPHAVIRUS PROTEIN E2

CROSS-REFERENCE TO RELATED APPLICATIONS

This application is a national stage entry under 35 U.S.C. §371 of PCT/EP2011/074121, filed on Dec. 28, 2011, which claims priority to U.S. Provisional Application No. 61/430,299, filed on Jan. 6, 2011; and EP Application No. 10197232.1, filed on Dec. 29, 2010. The content of PCT/EP2011/074121 is hereby incorporated by reference in its entirety.

REFERENCE TO SEQUENCE LISTING SUBMITTED ELECTRONICALLY

The sequence listing of the present application is submitted electronically via EFS-Web as an ASCII formatted sequence listing with a file name "2010029USPCT_SEQTXT_26JUNE2013", creation date of Jun. 17, 2013, and a size of 13.5 KB. This sequence listing submitted via EFS-Web is part of the specification and is herein incorporated by reference in its entirety.

The present invention relates to Salmonid alphavirus E2-protein expressed in a bacterial expression system, its use in medicine, vaccines comprising such protein, methods for the preparation of such proteins and methods for the preparation of vaccines comprising such proteins.

Pancreatic Disease (PD) is a serious disease that affects fish, in particular salmonid fish such as wild Atlantic salmon, rainbow trout and the like. The disease causes lesions in the pancreas, including loss of pancreatic exocrine tissue, and fibrosis, cardiac and skeletal muscle myopathies. Outbreaks of PD were first described in 1984 by Munro et al, in Helgoland (Meeresuntersuchungen 37:571-586 (1984)). PD typically affects the post-smolt fish during the first year after they are transferred to sea sites and is reported to spread rapidly among farm fish held in sea cages. Clinical signs include lethargy with a tendency to congregate in cage corners and to fail to maintain a horizontal position, cessation of feeding (anorexia) and significant mortalities (Ferguson et al, J. Fish Disease 9:95-98, 1986). Murphy et al (in J. Fish Disease 15:401-408, 1992) confirmed these observations in a later study, in which it was found that cardiac and skeletal myopathy is exacerbated in fish suffering from PD.

An outbreak of PD in a fish farm can cause growth to be reduced and up to 10 percent of surviving fish may prove to be runt. On Irish fish farms PD causes significant mortality rates of 10 to 60 percent among the young fish during the first year after they are transferred to sea sites (McLoughlin, M., Fish Farmer page 19, March/April 1995). The estimated cost to the Irish industry in terms of loss of production is currently thought to be around £25 million per year. Consequently, vaccines for the prevention and/or treatment of PD in fish have been developed and improved over the years.

European Patent EP712926 describes the isolation of the causative agent of PD from tissues of PD affected fish. This virus, know originally as Salmon Pancreas Disease virus (SPDV), is currently generally referred to as Salmonid Alphavirus (SAV). The abbreviation SAV will be used here to refer to this virus. To prevent PD infections in fish, the use of attenuated or inactivated PD for vaccination of the fish is accordingly suggested.

A drawback in the production of vaccines from the PD virus described in European Patent EP712926 is the slow growth of the virus, in particular on cell cultures, which makes the manufacturing of said vaccines a relatively inefficient process.

In European Patent EP1075523, ways of circumventing this point have been described. This patent discloses for the first time i.a. viral proteins and their amino acid sequences. In this patent, it is i.a. described how a SAV E2-protein can be used for the preparation of subunit vaccines for the protection of salmonid fish against SAV.

Such vaccines based upon SAV E2-protein preferably comprise the E2-protein as either a protein isolated from the virus or as a recombinant expression product made using a recombinant expression system. And since isolation of the E2-protein from the virus is time-consuming and expensive, recombinant expression of the protein would be the method of choice.

Bacterial expression systems would seem to be attractive systems since they are easy to use, inexpensive and produce relatively large amounts of protein. They do however have several drawbacks, i.a. the fact that they do not glycosylate the expressed protein, and the fact that the expression product is usually made in an undesirable form as densely packed insoluble protein molecules in the form of particles; so-called inclusion bodies. This may have impact on the biological and immunological properties of the protein.

The formation of such inclusion bodies has been countered in different ways. First the inclusion bodies have to be denatured and solubilised, for example by an initial solubilisation in e.g. high concentrations of urea, followed by a refolding step. An agent frequently used in refolding attempts of such solubilised molecules is the amino acid L-arginine. (Kouhei Tsumoto et al., Biotech Prog. 20: 1301-1308 (2004), Jing Chen et al., Biotech Prog. 24:1365-1372 (2008), Jing Chen et al., Protein expression and purification 66: 82-90 (2009)).

The consequences of inclusion body formation in bacterial expression systems vary depending on the nature of the protein. For some proteins, bacterial expression is useful, but if complex folding of the protein is necessary to maintain its activity, e.g. as an enzyme or as an immunogen, expression in bacterial expression systems usually turns out to be inadequate.

It is known that an alphavirus E2-protein when produced in bacterial expression systems, has only a quite low level of immunogenicity and high amounts are needed to induce an immune response. This is known for the E2-protein of the closely related Alphavirus Western Equine Encephalitis virus WEEV E2-protein (Das, D. et al., vide infra), and it is also shown for the SAV E2-protein in the Examples section, vide infra. And of course this has been mainly attributed to the fact that alpha viral E2-proteins, as most other proteins in bacterial expression system, form these undesirable inclusion bodies.

In an attempt to overcome this problem for WEEV, Das, D. et al., have refolded bacterially expressed E2-protein of the closely related Alphavirus WEEV in the presence of the amino acid L-arginine.

However they found that such E2-protein, even after denaturation in 6M urea followed by refolding in the presence of L-arginine, provides a very poor protection against WEEV infection in vivo, especially when compared to the protection provided by inactivated whole WEE virus.

In a later publication that further elaborated on the work by Das et al., Hu et al., conclude that E2-protein when expressed in a bacterial expression system, even after denaturation in 8M urea followed by refolding in the presence of L-arginine is only suitable for use in immunoassays, not as a vaccine component, due to lack of protection in vivo. (Das, D. et al., Virus Research 128: 26-33 (2007), Wei-Gang Hu et al., Veterinary Microbiology 128: 374-379 (2008)).

Therefore, recombinant E2 expression (and for that matter the expression of by far most other proteins) is preferably done in a non-bacterial expression system. Such non-bacterial expression systems are e.g. baculovirus expression systems, yeast-based expression systems and expression systems using mammalian cells.

It would however be desirable to have a SAV E2 protein that is expressed in a bacterial expression system and nevertheless is capable of inducing protection in fish against infection with Salmonid Alphavirus when used in a vaccine for the protection of salmonid fish against SAV infection.

It is an objective of the present invention to provide a SAV E2-protein that, although made in a bacterial expression system, is capable of inducing protection in fish against infection with Salmonid Alphavirus.

It was surprisingly found now, that the E2-protein of SAV when expressed in a bacterial expression system and after denaturation in urea followed by refolding in the presence of the amino acid L-arginine provides, in sharp contrast to the E2-protein of the very closely related Alphavirus WEEV, a highly immunogenic protein that is capable of inducing protection in fish against infection with Salmonid Alphavirus. This is also in sharp contrast to SAV E2-protein inclusion bodies, that are hardly or not capable of inducing protection in fish against infection with Salmonid Alphavirus.

Therefore, a first embodiment of the present invention relates to a Salmonid Alphavirus (SAV) E2-protein, characterised in that said SAV E2-protein is expressed in a bacterial expression system and capable of inducing protection in fish against infection with Salmonid Alphavirus, said SAV E2-protein being obtainable by a process comprising the steps of 1) expressing a DNA molecule comprising a gene encoding the Salmonid Alphavirus E2-protein in a bacterial expression system, 2) denaturing said protein and 3) refolding said protein in the presence of L-arginine.

The SAV E2-protein according to the invention is soluble in a watery environment, such as Phosphate Buffered Saline or a watery TRIS-buffer. The Examples section provides examples of such watery environments.

In nature, the structural proteins of SAV; the capsid protein, envelope proteins 1, 2 and 3 and the so called 6K protein are expressed as a polyprotein of about 130 kD in size. The order of the structural proteins in this polyprotein is "Capsid-E3-E2-6K-E1". This polyprotein is then proteolytically cleaved into the various structural proteins. (Weston, J. H., et al., Virology 256: 188-195 (1999) and European Patent EP 1075523).

An example of an amino acid sequence of a SAV E2-protein, (in this example preceded by part of the E3-protein), is given in SEQ ID NO.: 13, and its coding sequence is given SEQ ID NO.: 12.

The amino acid sequence of the SAV E3-protein starts at position 1 of SEQ ID NO.: 13 and ends with the amino acid Arg at position 65 (the first amino acids of E3; TRAPALLLLP (SEQ ID NO: 14) are not represented in this amino acid sequence). The SAV E2-protein starts with the amino acid Ala at position 66 and ends with the amino acid Ala at position 503.

It goes without saying that amino acid variants of the specific SAV E2-protein example in SEQ ID NO.: 13 are also incorporated in this invention In the genome of Pancreas Disease virus, small nucleic acid changes may occur that are currently used to determine the geographical niche of the virus. For ease of use, these PD viruses are indicated SAV subtype 1 (SAV1), SAV subtype 2 (SAV2) and so on. Therefore, merely as an example, the Salmonid Alphavirus E2-protein according to the invention can e.g. be of subtype SAV1, SAV2 or SAV3, since these subtypes give a very high level of (cross-) protection.

As mentioned (vide supra), SAV E2-protein inclusion bodies are either not or hardly immunogenic. Only in very high concentrations and in the presence of strong adjuvantia, inclusion bodies may induce some protection.

The soluble and L-arginine-refolded SAV E2-protein according to the invention however is capable of inducing protection when given in low amounts and with standard adjuvantia commonly used in fish vaccines.

Merely as an example, a vaccine comprising 130 µg of SAV E2-protein, denatured and refolded according to the invention, in Montanide ISA763A VG adjuvant (w/o ratio 30/70 w/w) provides a protection after intraperitoneal administration against challenge with wild-type SAV, of at least 75%, whereas a vaccine comprising 130 µg of SAV E2-protein in the form of inclusion bodies in the same adjuvant and also administered intraperitoneally, gives no protection at all, or at best a level of protection below 25%.

Thus, the wording "capable of inducing protection in fish against infection with Salmonid Alphavirus" should be understood as follows: the soluble and L-arginine-refolded SAV E2-protein according to the invention is capable of inducing protection of at least 75% relative percentage of protection (RPP) under conditions in which SAV E2-protein in the form of inclusion bodies induces a level of protection of less than 25% RPP. Protection is measured here as relative percentage of protection (RPP) as follows: fish presenting a heart lesion score higher or equal to 2 were considered as "infected" (they show specific PD lesions). Fish with scores of 0 or 1 were considered as "not infected". Relative percent protection (RPP) data was calculated using the formula: RPP=[1−(number of infected in vaccinated group/number of infected in unvaccinated group)])×100.

Refolding in the presence of L-arginine, for the purpose of this invention, means that a (partially or fully) denatured and thus (partially or fully) unfolded SAV E2-protein in an aqueous composition is allowed to refold in the presence of L-arginine.

Basically, the steps for obtaining such SAV E2-protein according to the invention comprise the following steps: bacteria expressing the SAV E2-protein are grown and the bacteria comprising the expressed SAV E2-protein as inclusion bodies are harvested e.g. by centrifugation, followed by the step of lysis of the bacteria, e.g. with lysozyme, and the isolation of the inclusion bodies. This isolation can easily be done by centrifugation.

The steps of growing bacteria expressing the SAV E2-protein and isolating the inclusion bodies are not critical. And these steps are well-known in the art.

Thereafter, denaturation of the protein can e.g. be done by mixing the pelleted inclusion bodies of the protein with a buffer comprising high concentrations of urea or guanidine chloride. Denaturation can e.g. be done by resuspending bacterial pellets in PBS buffer by sonification, followed by adding the sonicated solution to denaturation buffer. An example of a buffer that is suitable for denaturation, is a 100 mM Tris buffer pH 8.0 with 50 mM glycine and 8.5 M urea. After a next round of centrifugation in order to remove non-dissolved material, the supernatant comprises the denatured SAV E2-protein that is now ready for the refolding step.

Refolding can i.a. be done by rapid dilution of the denatured SAV E2-protein in an L-arginine buffer or through dialysis against an L-arginine buffer. A very suitable method is dialysis against a refolding buffer with 4 M urea for 48 hrs followed by dialysis against urea-free refolding buffer for 24 hrs. An example of a suitable refolding buffer is a buffer comprising 100 mM Tris buffer+0.4 M L-arginine.

The paper by Kouhei Tsumoto (vide supra) and the papers by Jing Chen (vide supra) give ample general guidance for refolding of proteins in general in the presence of L-arginine. Moreover, the Examples section below gives detailed instructions about how to realise both denaturation and refolding of the SAV E2-protein in the presence of L-arginine, especially with regard to e.g. the L-arginine concentration and buffer compositions.

Bacteria that are very suitable for the expression of the SAV E2-protein according to the invention are e.g. *Escherichia coli, Bacillus subtilis* and *Lactobacillus* species, in combination with bacterial expression vectors as pET, pGEX, or with bacteriophages.

Preferably, the bacterium used in the bacterial expression system is *E. coli*.

Bacterial expression systems are known in the art since decades already. And they are widely commercially available. Nevertheless, merely as an example: useful expression control sequences which may be used to drive the SAV E2-protein expression in bacteria include the Trp promoter and operator (Goeddel, et al., Nucl. Acids Res., 8, 4057, 1980); the lac promoter and operator (Chang, et al., Nature, 275, 615, 1978); the outer membrane protein promoter (Nakamura, K. and Inouge, M., EMBO J., 1, 771-775, 1982); the bacteriophage lambda promoters and operators (Remaut, E. et al., Nucl. Acids Res., 11, 4677-4688, 1983); the α-amylase (*B. subtilis*) promoter and operator, termination sequences and other expression enhancement and control sequences compatible with the selected host cell.

Handbooks giving extensive information about expression in bacterial expression systems are e.g.: *Manual of Industrial Microbiology and Biotechnology,* 3rd Edition by Richard H. Baltz (Editor-in-Chief), Arnold L. Demain (Editor-in-Chief), Julian E. Davies (Editor-in-Chief) ISBN: 978-1-55581-512-7, *E. coli* gene expression protocols by Peter E. Vaillancourt in Methods in Molecular Biology 205 ISBN: 1-58829-008-5, Protein expression: a practical approach by S. J. Higgins and B. D. Hames ISBN: 0-19-963624-9, *Protein expression technologies: current status and future trends,* 2004 by Francois Baneyx and *Production of recombinant proteins: novel microbial and eukaryotic expression systems* by Gerd Gellissen, ISBN: 3-527-31036-3.

The Examples section below gives further guidance concerning the expression of SAV E2-protein in bacteria.

It may be convenient to leave at least part of the SAV E3-protein gene in place at its native location, i.e. immediately upstream of the SAV E2-protein gene during the cloning process. There may be restriction sites located in the SAV E3-gene that may facilitate the construction of a suitable expression vector. Immunologically, the presence of a part or the whole SAV E3-protein is not necessary since in an in vivo situation the SAV E3-protein is enzymatically cleaved from the SAV E2-protein and if only for this reason, the SAV E3-protein is considered not to contribute to the immunogenic character of the SAV-E2 protein as such. Nevertheless the SAV E2-protein in a form in which at least part of the SAV E3-protein is still attached to it may possibly experience an advance in the process of refolding according described in the invention.

Thus, a form of this embodiment relates to Salmonid Alphavirus (SAV) E2-protein according to the invention characterised in that at least part of the SAV E3-protein is still attached to the SAV E2-protein.

Another embodiment of the present invention relates to a vaccine for the protection of salmonid fish against Salmonid Alphavirus infection, that comprises an immunogenic amount of Salmonid Alphavirus E2-protein according to the invention and a pharmaceutically acceptable carrier.

An immunogenic amount of Salmonid Alphavirus E2-protein is the amount of E2-protein that induces an immune response in fish that decreases the pathological effects of the disease after infection of that fish with a wild-type SAV, in comparison to the pathological effects in non-vaccinated fish after infection of that fish with a wild-type SAV.

Vaccines according to the present invention comprise, as said, a pharmaceutically acceptable carrier. A pharmaceutically acceptable carrier can be e.g. sterile water or a sterile physiological salt solution. In a more complex form the carrier can e.g. be a buffer.

Vaccines according to the present invention may in a preferred presentation also contain an immunostimulatory substance, a so-called adjuvant. Adjuvants in general comprise substances that boost the immune response of the host in a non-specific manner. A number of different adjuvants are known in the art. Examples of adjuvants frequently used in fish and shellfish farming are muramyl dipeptides, lipopolysaccharides, several glucans and glycans and Carbopol® (a homopolymer). An extensive overview of adjuvants suitable for fish and shellfish vaccines is given in the review paper by Jan Raa (Reviews in Fisheries Science 4(3): 229-288 (1996)). Frequently used adjuvants in fish vaccines are so-called water-in-oil adjuvantia. The oil used in such o/w adjuvantia is often a non-mineral oil, such as Montanide™ ISA 763A.

The vaccine may also comprise a so-called "vehicle". A vehicle is a compound to which the protein adheres, without being covalently bound to it. Such vehicles are i.a. bio-microcapsules, micro-alginates, liposomes and macrosols, all known in the art. A special form of such a vehicle, in which the antigen is partially embedded in the vehicle, is the so-called ISCOM (EP 109.942, EP 180.564, EP 242.380)

In addition, the vaccine may comprise one or more suitable surface-active compounds or emulsifiers, e.g. Span or Tween.

Often, the vaccine is mixed with stabilisers, e.g. to protect degradation-prone proteins from being degraded, to enhance the shelf-life of the vaccine, or to improve freeze-drying efficiency. Useful stabilisers are i.a. SPGA (Bovarnik et al; J. Bacteriology 59: 509 (1950)), carbohydrates e.g. sorbitol, mannitol, trehalose, starch, sucrose, dextran or glucose, proteins such as albumin or casein or degradation products thereof, and buffers, such as alkali metal phosphates.

In addition, the vaccine may be suspended in a physiologically acceptable diluent.

The vaccines according to the invention may be stored in a freeze-dried form. Freeze-dried proteins have a much longer shelf-live, especially at room temperature, when compared to the a liquid form. The process of freeze-drying as such is extensively known in the art.

It goes without saying, that other ways of adjuvating, adding vehicle compounds or diluents, emulsifying or stabilising a protein are also comprised in the present invention.

Vaccines according to the invention that comprise the SAV E2-protein according to the invention can very suitably be administered in amounts comprising between 10 and 1000 micrograms of SAV E2-protein per dose, although lower doses can in principle be used. An adjuvant helps to lower the amount of SAV E2-protein that has to be administered.

A dose exceeding 1000 micrograms could, although immunologically very suitable, be less attractive for commercial reasons.

More preferably, the amount of SAV E2-protein is between 100 and 300 micrograms per dose.

The volume of injection fluid in a dose, i.e. the total amount of fluid administered to the animal including the antigen, the pharmaceutically acceptable carrier and possibly an adjuvant and other excipients preferably varies between 50 and 200 microliter. Smaller amounts could possibly cause aggregation of some of the components whereas larger amounts could be physically too stressful for the animal.

Many ways of administration, all known in the art can be applied. The protein-based vaccines according to the invention are preferably administered to the fish via injection, immersion, dipping or per oral. The administration protocol can be optimized in accordance with standard vaccination practice. Preferably the vaccine is administered via immersion or per oral, especially in case of commercial aqua culture farms.

For oral administration the vaccine is preferably mixed with a suitable carrier for oral administration i.e. cellulose, food or a metabolisable substance such as alpha-cellulose or different oils of vegetable or animals origin. Also an attractive way of administration is administration of the vaccine to high concentrations of live-feed organisms, followed by feeding the live-feed organisms to the target animal, e.g. the fish. Particularly preferred food carriers for oral delivery of the vaccine according to the invention are live-feed organisms which are able to encapsulate the vaccine.

Salmonid fish are usually not only vaccinated against Salmon Pancreatic Disease virus, but also against several other infectious diseases. The administration of the various vaccines should, if possible, preferably be done at one and the same moment. This can easily be done through administration of a combination vaccine. Such a combination vaccine would then comprise a SAV E2-protein according to the invention and an immunogenic amount of at least one other antigenic component or genetic information encoding such an antigenic component.

Analogous to the definition given above for SAV E2-protein, an immunogenic amount of that antigenic component is the amount of that component that induces an immune response in fish that decreases the pathological effects of the disease after infection of that fish with a wild-type pathogen, in comparison to the pathological effects in non-vaccinated fish after infection of that fish with a wild-type pathogen.

In general, the term antigenic component refers to a composition of matter that comprises at least one epitope that can induce, stimulate or enhance an immune response when administered to a human or an animal.

The antigenic component may be any kind of antigenic component but preferably is derived from a micro-organism or virus that in its wild-type form is pathogenic to fish.

The antigenic component can be the whole pathogen, preferably in an inactivated or attenuated form, an extract of the pathogen or an immunogenic protein of the pathogen.

If the antigenic component is an immunogenic protein of the pathogen, that immunogenic protein is preferably expressed in and recovered from in vitro cultured cells.

Therefore, another embodiment relates to a vaccine for the protection of salmonid fish against Salmonid Alphavirus infection according to the invention characterised in that said vaccine additionally comprises an immunogenic amount of at least one other antigenic component or genetic information encoding such an antigenic component.

Preferably the antigenic component is, or is derived from a virus or micro-organism that in its wild-type form is pathogenic to fish.

Such an antigenic component can be e.g. another SAV antigen. It can also be an antigenic component selected from other fish pathogenic organisms and viruses, or it can be a whole fish pathogenic organism or virus. Such organisms and viruses are preferably selected from the group of aquatic birnaviruses such as infectious pancreatic necrosis virus (IPNV), aquatic nodaviruses such as striped jack nervous necrosis virus (SJNNV), aquatic rhabdoviruses such as infectious haematopoietic necrosis virus (IHNV) and viral haemorrhagic septicaemia virus (VHSV), Pancreas Disease virus (SPDV) and aquatic Orthomyxoviruses such as infectious salmon anaemia virus (ISAV) and the group of fish pathogenic bacteria such as *Flexibacter columnaris, Edwardsialla ictaluri, E. tarda, Yersinia ruckeri, Pasteurella piscicida, Vibrio anguillarum, Aeromonas salmonicida* and *Renibacterium salmoninarum.*

Again another embodiment of the present invention relates to a method for the preparation of a Salmonid Alphavirus E2-protein according to the invention wherein said method comprises the steps of 1) expressing a DNA comprising a gene encoding a Salmonid Alphavirus E2-protein in a bacterial expression system, 2) denaturing said protein and 3) refolding said protein in the presence of L-arginine.

Still another embodiment of the present invention relates to methods for the preparation of a vaccine comprising Salmonid Alphavirus E2-protein according to the invention, wherein said method comprises the step of mixing Salmonid Alphavirus E2-protein according to the invention and a pharmaceutically acceptable carrier.

A further embodiment of the present invention relates to Salmonid Alphavirus E2-protein according to the invention for use as a medicament Still another embodiment of the present invention relates to Salmonid Alphavirus E2-protein according to the invention for use in the protection of salmonid fish against Salmonid Alphavirus virus infection.

The following examples are merely illustrative for the invention and should not be interpreted as limitations of the invention.

EXAMPLES

Example 1

Cloning Strategy of SAV E2 (Norwegian Isolate) in pET30a for Recombinant Expression in *E. Coli*

A SAV coding sequence encoding the SAV E2-gene and part of the E3-protein but lacking the fragment encoding the 5' amino acids TRAPALLLLP (SEQ ID NO: 14) was obtained from a Norwegian SAV isolate subtype 3 as follows: a SAV infected Atlantic salmon was sampled from an aquaculture farm in Norway (Mølsvik). From its heart tissue a total RNA extract was prepared using an "Absolutely RNA miniprep kit" (Stratagene), according to the manufacturer's instructions. From the cDNA prepared, the total E3E2 coding region was amplified with RT-PCR primers.

For the reverse transcription, the following primer was used:

(SEQ ID NO: 1)
RTE2:    5'- CCGCGCGAGCCCCTGGTATGCAACACAGTGC -3'

Next, high fidelity PCR amplification was performed, using pfu turbo polymerase (Stratagene), with the primer set:

```
RT-E2 XhoI:
                                        (SEQ ID NO: 2)
5'- ATACCAGGGGCTCGCGCCTCGAGACCCTACTTG -3'

PCR-E3 HindIII:
                                        (SEQ ID NO: 3)
5'- GATGCCATAAGCTTGACACGCGCTCCGGCCCTC -3'
```

The blunt PCR product obtained was then A-tailed following incubation with Taq polymerase, dATP, 1× reaction buffer and $MgCl_2$ (Promega) during 30 min at 70° C.

The A-tailed PCR product was then cloned in the vector PCR 2.1-Topo (Invitrogen) according to the manufacturer's instructions.

Finally the sequence of the cloned E3E2 insert was determined by sequencing with the two PCR primers, and two internal primers:

```
                                        (SEQ ID NO: 4)
PD5:    5'- CGTCACTTTCACCAGCGACTCCCAGACG -3'

(SEQ ID NO: 5)
PD3:    5'- GGATCCATTCGGATGTGGCGTTGCTATGG -3'
```

Sequencing was performed with Big Dye 3.1® (Applied Biosystems), according to the manufacturer's instructions.

Once verified by sequencing, the E3E2 PCR product was digested overnight with the restriction enzymes XhoI and HindIII, and cloned in the corresponding unique sites of the pET30a(+) vector (Novagen) leading to the construct pET30a/E3E2.

In order to remove the unwanted N-terminal histidine tag sequence from the pET30a vector flanking the E3E2 insert in 5', a mutagenesis adding an NdeI site in the E3 sequence was performed on the pET30a/E3E2 construct using the following primers:

```
E3/NdeI-FWD:
                                        (SEQ ID NO: 6)
5'-CCCTCCTGCTGCTGCATATGGTTATTGTCTGCACC-3'

E3/NdeI-REV:
                                        (SEQ ID NO: 7)
5'-GGTGCAGACAATAACCATATGCAGCAGCAGGAGGG-3'
```

This mutated construct was then digested overnight with the restriction enzyme NdeI, purified from an agarose gel (Strataprep DNA gel extraction kit, Stratagene), and ligated overnight using T4 DNA ligase kit (Promega) according to manufacturer's instructions. This construct was thus rendered devoid of the N-terminal histidine tag encoding sequence.

An additional mutagenesis was performed on this last construct in order to add a stop codon at the 3' end of the E3E2 insert sequence, in front of the C-terminal histidine tag encoding sequence. To do so, the following mutagenesis primers were used:

```
MutE2StopF:
                                        (SEQ ID NO: 8)
5'-GCATACCTGGGGCTCGTGCGTGACAACCCTACCTGGACATC-3'

MutE2StopR:
                                        (SEQ ID NO: 9)
5'-GATGTCCAGGTAGGGTTGTCACGCACGAGCCCCAGGTATGC-3'
```

The final construct was named "pET30a/E3E2 ΔHis C". Its insert's sequence was verified by DNA sequencing using the standard pET-T7 promoter primer: 5'-AATACGACTCAC-TATAGGG-3' (SEQ ID NO: 10) and standard T7 terminator primer: 5'-GCTAGTTATTGCTCAGCGG-3' (SEQ ID NO: 11) in order to obtain overlapping contigs covering the whole cloned sequence. The nucleotide sequence of the E3E2 encoding region cloned in pET30a/E3E2 ΔHis C is given in SEQ ID NO.: 12. The amino acid sequence of the E3E2 protein encoded by the nucleotide sequence depicted in SEQ ID NO.: 12 is given in SEQ ID NO.: 13. For reasons of ease of cloning, part of the E3-sequence was left present during the cloning process. This is however not necessary. As discussed (vide supra) in an in vivo situation the E3 protein is enzymatically cleaved from the E2 protein and if only for this reason, the E3 protein is considered not to contribute to the immunogenic character of the E2 protein. For this reason, the protein that is expressed by the plasmid pET30a/E3E2 ΔHis C will, although it still comprises part of the E3-protein, further be referred to as a SAV E2-protein.

Example 2

Preparation of *E. Coli* SAV E2 Protein and Inclusion Bodies Purification

Expression:

An overnight pre-culture (20 ml) of an *E. coli* strain carrying the pET construct was prepared (pET30a/E3E24His-C construct in *E. coli* Rosetta 2 cells).

Thereafter, 4×800 ml Luria Broth medium+kanamycin were inoculated with 5 ml pre-culture. Up to 1 mM (final conc.) IPTG was added as soon as the OD600 reached 0.7

The induction of expression was left ongoing for 2 hours

Next, the cultures were divided in four bottles and centrifuged at 7000 rpm for 5 min.

The pellet was kept at −80° C. until use.

Purification:

The following buffers were made:

buffer *A*=50 mM tris/HCl pH8.00+2 mM EDTA buffer *B*=buffer *A*+1% (final concentration) Triton X-100

The pellets of each of the 800 ml cultures above were resuspended in 50 ml of buffer A and freshly prepared lysozyme (stock at 10 mg/ml) was added to a final concentration of 100 microgram/ml. Subsequently, 25 ml of buffer B was added.

Thereafter, 10 microliters of Benzonase (MERCK, 10.000 u/vial) were added and the fluid was incubated at 30° C. for 15 min. with gentle shaking for the removal of DNA.

Then, 100 ml of buffer B was added and the fluid was sonicated for 4×30 seconds (max. intensity).

The fluid was subsequently centrifuged at 12.000 g for 20 min. at 4° C., the inclusion body pellet was washed three times with 250 ml of buffer B, and thereafter washed three times with 200 ml of PBS Finally, the pellets were resuspended in 40 ml (4×10 ml) of PBS and kept at −80° C. until use.

Example 3

Denaturing and Refolding of SAV E2 Protein from Inclusion Bodies

Denaturing Buffer:

100 mM Tris buffer pH 8.0+50 mM glycine+8.5 M urea

A 100 ml of this buffer was prepared by mixing:

10 ml of 1 M Tris buffer pH 8.0

375 mg glycine (75 g/mol)

51 g urea (60.06 g/mol)

De-ionized water to reach 100 ml.

Refolding Buffer (RF):
100 mM Tris buffer+0.4 M L-arginine.
A 2 liter preparation was made by mixing:
200 ml of 1 M Tris buffer pH 8.0
139.4 g L-arginine (174.20 g/mol)
De-ionized water to reach 2 liters.

Protocol:

The preparation of inclusion bodies, starting from 5 ml of a 6 mg/ml inclusion body solution comprised the following steps:

1) Sonication of 5 ml E2 inclusion bodies at 6 mg/ml (total=30 mg) was done to disperse the pellet completely (30" pulses, on ice).
2) the inclusion bodies were diluted to a concentration of 1 mg/ml by adding the 5 ml sonicated IB suspension drop wise, while stirring vigorously, to 25 ml denaturing buffer.
3) Then 5 mM GSH (glutathione reduced) (46.1 mg for 30 ml; 307.33 g/mol)+0.5 mM GSSG (glutathione oxidized) (9.1875 mg for 30 ml; 612.6 g/mol) were added and stirred overnight at 4 C.
4) The fluid was then centrifuge 30' at 3000 rpm (1831×g) to remove insoluble material and the supernatant was transferred to a new tube.
5) The supernatant was dialysed (Slide-a-Lyzer Pierce cassette, 2 KD cut-off) for 48 hrs against 1 liter RF buffer+4 M urea (242.4 g for 1 liter RF buffer) at 4 C.
6) Thereafter the supernatant was dialysed for 24 hrs against 1 liter RF buffer at 4 C.
7) Then the supernatant was dialysed for 24 hrs against 1 liter TBS 1× at 4 C.
8) Next, the protein in solution was collected from the dialysis cassette and centrifuged for 20 minutes at 13000 rpm (12000×g) to remove precipitate.
9) Solubilized protein was analysed on SDS-PAGE and quantified. If necessary, the solubilised protein was up-concentrated with vivaspin 20 (3 KD cut-off) columns (Sartorius: Vivaspin 20, 3000 MWCO).

Example 4

4.1.1. Recombinant and Inactivated Antigens

Recombinant E. Coli SAV E2 Refolded

The soluble and refolded SAV E2-protein as obtained according to Examples 1-3 was concentrated by filtration using a Vivaspin 20 tube (cut-off=30 KDa), reducing the volume to 4.5 ml with a concentration of 2.4 mg/ml.

This suspension was stored at −80° C. until vaccine formulation.

Saline (Negative Control)

Saline solution (0.9% NaCl) was used as a negative control.

4.1.2. Quantification of the Antigens

All the recombinant test antigens were quantified relatively to a Bovine Serum Albumin standard by scanning and densitometric analysis of Coomassie stained gel with the Molecular Analyst program.

4.1.3. Formulation of Test Vaccines

The vaccine formulation was produced based on Montanide™ ISA 763A VG emulsions

A low-shear ISA 763A emulsion with the antigens produced in *E. coli* was obtained by mixing with a propeller the ISA763A oil phase and the water phase containing the antigen during 10 minutes at 1300 rpm.

The *E. coli* produced SAV E2-Rf (re-folded) antigen comprised 130 μg antigen in a total volume of 200 μl (adjuvant =ISA763A VG; W/O ratio=30/70 w/w).

4.1.4. Vaccination

All fish were labelled and vaccinated by intraperitoneal injection with the doses of their respective vaccines as indicated in table 1.

TABLE 1

Test articles, group numbering/labelling and composition per dose:

| Group no. | Expression system | Antigen | Antigen concentration/ dose | No. of doses |
|---|---|---|---|---|
| 1 | *E. coli* | E2 refolded (soluble) | 130 μg/200 μl | 42 |
| 2 | — | Saline (negative control) | 100 μl | 42 |

4.1.5 Challenge Material

A Norwegian SAV subtype 3 isolate propagated to second passage in CHSE-214 cell culture was used for challenge. One aliquot (0.5 ml) stored in liquid nitrogen was thawed, diluted 1:20 in EMEM medium and kept on ice until challenge within 2 hours.

4.2. TEST SYSTEM

4.2.1. Experimental Fish

Commercially available Atlantic salmon was used. Fish weight: 30+/−5 g. Sex: mixed. Only IPNV free populations were used. The experimental population was acclimatised at least one week before the experiment is started. Only healthy fish was included in the study. The experimental groups were taken from a reservoir and kept in freshwater tanks. After vaccination, treatment of sick animals was not undertaken.

4.2.2 Husbandry

Salinity: 0%

Temperature: 10-13° C.

pH: 6.3-6.9

Oxygen: >65% saturation

Tank size: 500 l

Feeding: According to appetite

Density max 20 $kg/m^3$

The following treatment schedule was carried out during the establishment of the experimental groups:

Starvation: 24 hours before each handling of the fish

Anaesthetics: Metacainum 0.1 mg/ml, bath treatment for 2-3 min. before each handling of the fish Vaccination: Intra-peritoneal injection of oil adjuvanted vaccine or saline (100 or 200 μl; cf Table 1).

4.3. EXPERIMENTAL PROCEDURES

4.3.1. Overview and Sampling Protocol

TABLE 2

Overview of the experiment.
Operation (no. of fish sampled)

Vaccination 42 fish/group
Cohab. SAV3 challenge at 8 weeks post vaccination.
Add 74 shedders IP injected with SAV3.
Histology + PCR sampling 5 wpc.
Sample heart for histology and PCR analysis (15 fish/group).

4.3.2. Vaccination Protocol

On the day prior to vaccination, the fish in the reservoir tank were starved.

On the following day, groups of 42 pre-smolts were netted out (in aliquots) from the reservoir tank and anaesthetised. The fish were then injected i.p. (100 µl or 200 according to table 1) with the test vaccines. After vaccination, the fish were placed in another tank where they remained until SAV3 challenge by cohabitation, 8 weeks later.

4.4 CHALLENGE PROTOCOL

4.4.1 Challenge 8 weeks post vaccination, the vaccinated fish (42 fish/group) were transferred to the challenge lab. Then 74 fish from the reservoir tank were transferred to the challenge lab and injected with 0.2 ml SAV3 challenge strain. These 74 IP injected shedders were then added to the vaccinated fish in order to perform the challenge by cohabitation.

4.4.2 Sampling and Examination

At 5 wpc, hearts were sampled from 15 fish/group and immediately fixed in 3.5% formaldehyde in buffered saline with pH 7.0 (4.0 g $NaH_2PO_4 2H_2O$, 6.5 g $Na_2HPO_4.2H_2O$, 100 ml 35% formaldehyde and 900 ml distilled water) prior to further processing and histological scoring analysis. Simultaneously small pieces of heart tissue were collected in individual tubes containing RNAlater solution for eventual SAV real-time RT-PCR analysis. Following one night at 4° C., these tubes were then stored at −80° C.

4.5.1. Histology

Histopathological lesions in heart tissue were examined. A score system was used to evaluate the severity of SPD-virus induced lesions in heart tissue (no: 0, minimal: 1, mild: 2, moderate: 3, severe: 4). Score 2 or higher is defined as SPD virus-specific. Both sampling points were evaluated and all test groups were compared to saline controls.

4.5.2. SAV Real-Time RT-PCR on Heart RNA

In order to detect the RNA from the SAV3 challenge strain in heart tissue during the viraemic phase (3-4 wpc), SAV real-time RT-PCR was performed on total RNA extracted from serum using QIAGEN RNAeasy 96 kit, according to the manufacturer's protocol. This RNA was submitted to a standardized real-time SAV specific RT-PCR (ABgene Verso™ 1-Step RT-PCR Kit AB-1454/A) assay in order to amplify viral RNA whenever the fish serum contains SAV. For this purpose, primers pair named nsP1-F/nsP1-R and TaqMan probe named nsP1 probe were used as described in Hodneland & Endresen (J. Virol Meth. 2006, 131(184-192)). Positive (RNA from SAV infected serum) and negative (RNA from SAV free serum) controls were included in the PCR.

Amplifications of the RT-PCR products following 40 amplification cycles were monitored using an ABI PRISM® 7500 Fast Sequence Detection System machine. A threshold line was defined within the common exponential region of the observed amplification curves. For positive fish, an exponential PCR amplification curve was observed and a Ct value was given. Samples without a Ct value in the SAV analysis were considered negative.

4.6. EVALUATION OF TEST RESULTS

4.6.1. Test Parameters for Evaluation of Efficacy

PD efficacy (protective capacity) of the different test formulations was evaluated by histopathology score. Both sampling points were evaluated and all test groups were compared to the saline control group.

The presence of SAV in heart at 5 wpc was evaluated categorically (+ or −) and relative difference between individual test groups and the control group calculated as Relative Percent protection (RPP, see under 4.6.2.).

4.6.2. Statistical Evaluation

Statistically differences in heart lesions, scored on the ordinal scale (0-4), between the test groups and the selected control group was statistically evaluated by Kruskall-Wallis Rank sum test with $p<0.05$ as significance limit. Dunn's test was used to perform pairwise comparison of the groups (Both tests were performed using SAS enterprise guide 4).

Fish presenting a heart lesion score higher or equal to 2 were considered as "infected" (specific PD lesions). Fish with scores lower than 2 were considered as "not infected".

Relative percent protection (RPP) data was calculated using the formula:

RPP=[1−(number of infected in vaccinated group/
number of infected in unvaccinated group)]×100

4.7. RESULTS AND DISCUSSION

4.7.1. Histology Results

The cardiac lesions scores evaluated following histological examination of 15 individual heart tissues sampled for each group 5 wpc are shown in table 3.

TABLE 3

Results of histological examination and lesion scores
of heart at 5 weeks post challenge.

| | 1 E2 refolded | | 2 Saline |
|---|---|---|---|
| Fish | Heart | Fish | Heart |
| 5301 | 0 | 5701 | 0 |
| 5302 | 0 | 5702 | 2 |
| 5303 | 0 | 5703 | 1 |
| 5304 | 0 | 5704 | 3 |
| 5305 | 0 | 5705 | 0 |
| 5306 | 0 | 5706 | 2 |

TABLE 3-continued

Results of histological examination and lesion scores of heart at 5 weeks post challenge.

| Fish | 1<br>E2 refolded<br>Heart | Fish | 2<br>Saline<br>Heart |
|---|---|---|---|
| 5307 | 0 | 5707 | 2 |
| 5308 | 0 | 5708 | 1 |
| 5309 | 0 | 5709 | 2 |
| 5310 | 0 | 5710 | 2 |
| 5311 | 2 | 5711 | 0 |
| 5312 | 0 | 5712 | 0 |
| 5313 | 0 | 5713 | 3 |
| 5314 | 0 | 5714 | 4 |
| 5315 | 0 | 5715 | 1 |
| | 6.7% positives | | 53.3% positives |

The histology data shown in table 3 showed that the PD cohabitant challenge was valid (although challenge pressure was low) for the 5 wpc sampling point, since prevalence of PD positive fish (score higher or equal to 2) in the saline group is 53.3% (8 fish positive out of 15).

RPP values can be calculated using these histology results at 5 wpc:

TABLE 4

Relative Percent Protection based on the prevalence of fish positive according to histological analysis of heart lesions.

| Group | E2 refolded |
|---|---|
| RPP (%) | 87.5 |

The test group vaccinated with refolded E2 expressed in *E. coli*, had a RPP of 87.5%.

4.7.2. SAV nsP1 Real-Time RT-PCR Detection on Heart Sampled at 5 Wpc

We performed a SAV nsP1 real-time RT-PCR assay on heart samples which had been collected in RNAlater (Ambion Inc.) at 5 wpc at the same time as the heart samples for histology, in order to see if the prevalence of fish positive for the presence of SAV genome in the heart correlated with the histology results. The results of this real-time RT-PCR assay are shown in table 5. RPP values were calculated based on these results and are shown in table 6.

TABLE 5

Results of SAV real-time RT-PCR universal nsP1 assay on heart at 5 wpc.

| Group | Antigen | Number of nsP1 positive fish/<br>total number of fish |
|---|---|---|
| 1 | E2 refolded (soluble) | 3+/15 |
| 2 | Saline | 12+/15 |

TABLE 6

RPP values determined for the test groups based on the results of SAV nsP1 realtime RT- PCR detection on heart sampled at 5 wpc.

| Group | E2 refolded |
|---|---|
| RPP % | 75 |

The results of the SAV real-time RT-PCR assay on hearts sampled at 5 wpc correlate well with the histology results at the same sampling point. The saline group present 80% of fish positive for the presence of SAV3 in the heart, and the group which shows the lowest prevalence and highest RPP is group 1 (20% prevalence, RPP=75%), which correlates well with the histology results at the same time point.

4.8. CONCLUSION

The aim of this PD efficacy study was to determine whether *E. coli* expressed, solubilised and L-arginine refolded SAV3 E2 glycoprotein could induce protection following a cohabitant SAV3 challenge.

The histological analysis of PD induced heart lesions indicated that the challenge was valid.

The histology results for 5 wpc clearly indicated than the refolded E2 produced in *E. coli*, induced high protection against the SAV3 cohabitant challenge, with an RPP value of 87.5%.

The results of SAV real-time RT-PCR assay performed on total RNA from heart tissues collected at 5 wpc clearly correlated the histological results, also indicating that the refolded E2 performed very good in this study.

The invention claimed is:

1. A Salmonid Alphavirus (SAV) E2-protein obtained by a process comprising the steps of:
   1) expressing a DNA molecule comprising a gene encoding the Salmonid Alphavirus E2-protein in a bacterial expression system,
   2) denaturing said protein and
   3) refolding said protein in the presence of L-arginine; wherein said SAV E2-protein is capable of inducing protection in fish against infection with Salmonid Alphavirus.

2. The Salmonid Alphavirus E2-protein of claim 1, wherein the bacterium used in the bacterial expression system is *E. coli*.

3. The Salmonid Alphavirus E2-protein of claim 2, wherein at least part of a SAV E3-protein is still attached to the E2-protein.

4. A method of protecting a fish against Salmonid Alphavirus virus (SAV) infection comprising administering said Salmonid Alphavirus E2-protein of claim 2 to the fish.

5. A vaccine for the protection of salmonid fish against Salmonid Alphavirus infection, wherein said vaccine comprises an immunogenic amount of Salmonid Alphavirus E2-protein of claim 2 and a pharmaceutically acceptable carrier.

6. The Salmonid Alphavirus E2-protein of claim 1, wherein at least part of a SAV E3-protein is still attached to the E2-protein.

7. A method of protecting a fish against Salmonid Alphavirus virus (SAV) infection comprising administering said Salmonid Alphavirus E2-protein of claim 6 to the fish.

8. A vaccine for the protection of salmonid fish against Salmonid Alphavirus infection, wherein said vaccine comprises an immunogenic amount of Salmonid Alphavirus E2-protein of claim 3 and a pharmaceutically acceptable carrier.

9. A method of protecting a fish against Salmonid Alphavirus virus (SAV) infection comprising administering said Salmonid Alphavirus E2-protein of claim 1 to the fish.

10. A vaccine for the protection of salmonid fish against Salmonid Alphavirus infection, wherein said vaccine comprises an immunogenic amount of Salmonid Alphavirus E2-protein of claim 1 and a pharmaceutically acceptable carrier.

11. The vaccine of claim 10, wherein said vaccine comprises an adjuvant.

12. The vaccine of claim 11, wherein said vaccine additionally comprises an immunogenic amount of at least one other antigenic component or genetic information encoding such an antigenic component.

13. The vaccine of claim 12, wherein said other antigenic component or genetic information encoding such an antigenic component is selected from the group consisting of infectious pancreatic necrosis virus (IPNV), striped jack nervous necrosis virus (SJNNV), infectious haematopoietic necrosis virus (IHNV), viral haemorrhagic septicaemia virus (VHSV), Pancreas Disease virus (SPDV), infectious salmon anaemia virus (ISAV), *Flexibacter columnaris, Edwardsialla ictaluri, E. tarda, Yersinia ruckeri, Pasteurella piscicida, Vibrio anguillarum, Aeromonas salmonicida* and *Renibacterium salmoninarum*.

14. A method for preparing a vaccine comprising the Salmonid Alphavirus E2-protein of claim 11, comprising mixing said Salmonid Alphavirus E2-protein with a pharmaceutically acceptable carrier.

15. The vaccine of claim 10, wherein said vaccine additionally comprises an immunogenic amount of at least one other antigenic component or genetic information encoding such an antigenic component.

16. The vaccine of claim 15, wherein said other antigenic component or genetic information encoding such an antigenic component is selected from the group of infectious pancreatic necrosis virus (IPNV), striped jack nervous necrosis virus (SJNNV), infectious haematopoietic necrosis virus (IHNV), viral haemorrhagic septicaemia virus (VHSV), Pancreas Disease virus (SPDV), infectious salmon anaemia virus (ISAV), *Flexibacter columnaris, Edwardsialla ictaluri, E. tarda, Yersinia ruckeri, Pasteurella piscicida, Vibrio anguillarum, Aeromonas salmonicida* and *Renibacterium salmoninarum*.

17. A method for preparing a vaccine comprising the Salmonid Alphavirus E2-protein of claim 15, comprising mixing said Salmonid Alphavirus E2-protein with a pharmaceutically acceptable carrier.

18. A method for preparing a vaccine comprising the Salmonid Alphavirus E2-protein of claim 10, comprising mixing said Salmonid Alphavirus E2-protein with a pharmaceutically acceptable carrier.

19. A method for the preparation of a Salmonid Alphavirus E2-protein of claim 1, wherein said method comprises the steps of:
1) expressing a DNA comprising a gene encoding a Salmonid Alphavirus E2-protein in a bacterial expression system,
2) denaturing said protein and
3) refolding said protein in the presence of L-arginine.

* * * * *